United States Patent [19]

Joa

[11] 4,162,019
[45] Jul. 24, 1979

[54] APPARATUS FOR RECOVERING FILLER FROM SANITARY PADS

[76] Inventor: Curt G. Joa, P.O. Box 1121, Boynton, Fla. 33435

[21] Appl. No.: 837,125

[22] Filed: Sep. 28, 1977

[51] Int. Cl.² .............................................. B65G 65/04
[52] U.S. Cl. ..................................... 414/412; 15/308; 241/235
[58] Field of Search .................. 214/304, 305; 15/308; 221/25, 30, 31; 241/235

[56] References Cited

U.S. PATENT DOCUMENTS

| 3,132,629 | 5/1964 | Krupotich | 214/304 |
| 3,340,789 | 9/1967 | Simjian | 221/25 |
| 3,395,042 | 7/1968 | Herbert, Jr. | 15/308 |

FOREIGN PATENT DOCUMENTS 860028  2/1961  United Kingdom .................... 214/305

Primary Examiner—Lawrence J. Oresky
Attorney, Agent, or Firm—Joseph P. House, Jr.

[57] ABSTRACT

Method and apparatus of recovering filler from a sanitary pad. The pad typically has a film backing and a cover sheet and filler therebetween. Such a pad is laid out flat and advanced through a cutter which opens up the cover to expose the filler. The filler is sucked from the pad for salvage and the film backing is discarded.

7 Claims, 5 Drawing Figures

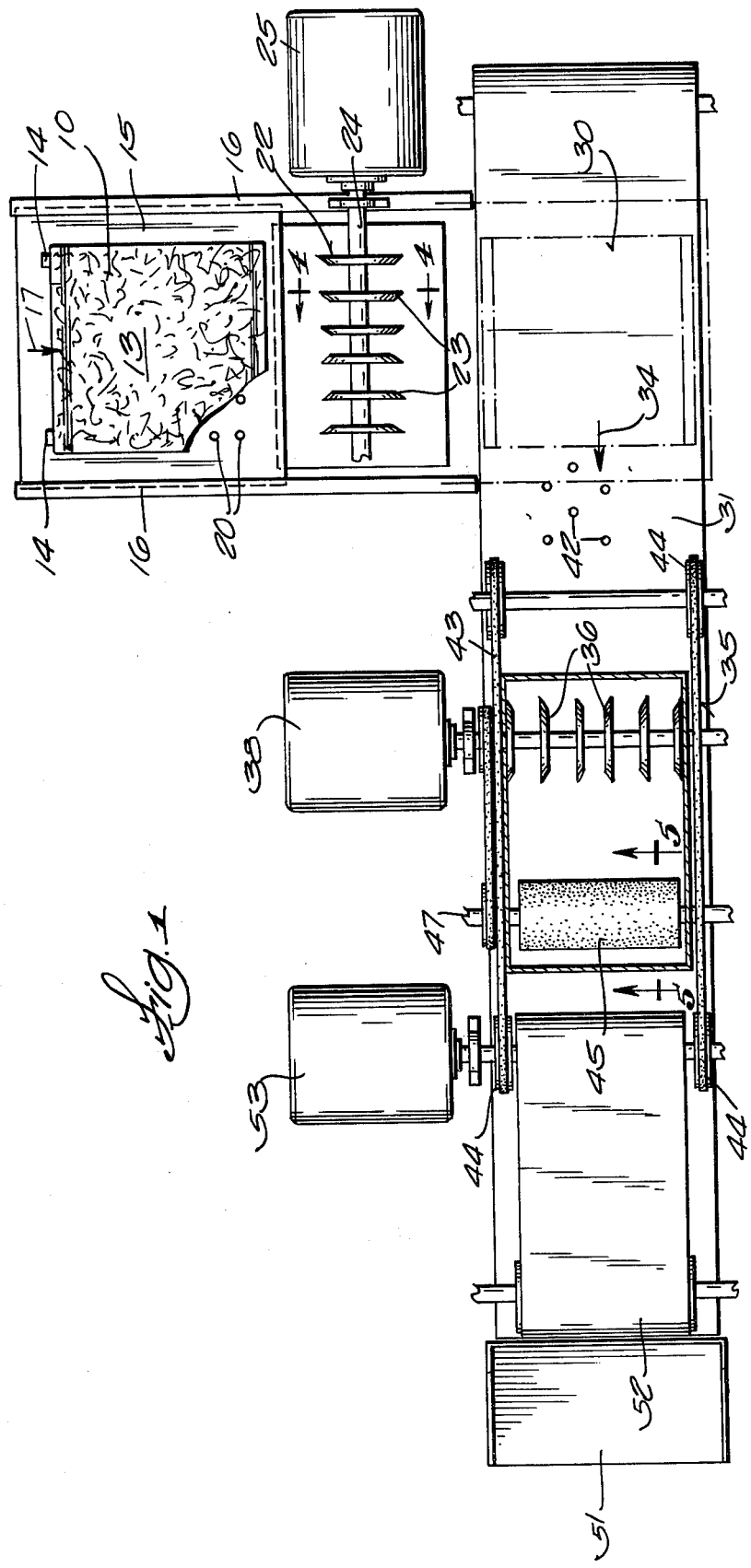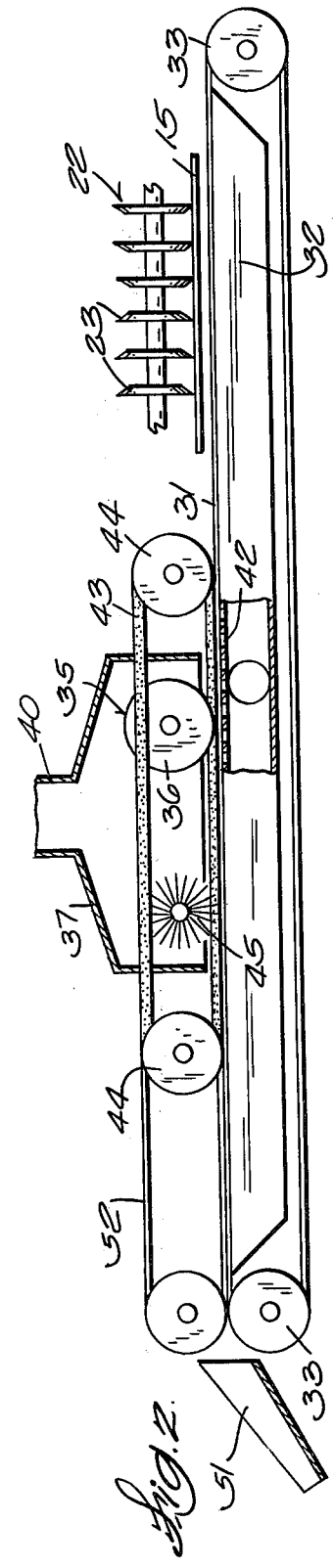

APPARATUS FOR RECOVERING FILLER FROM SANITARY PADS

BACKGROUND OF THE INVENTION

In the fabrication of sanitary pads such as sanitary napkins, hospital pads, disposable diapers and the like, a certain percentage of the pads will be defective and are discarded. While the filler material utilized in such pads, typically cellulose fluff, constitutes high quality reusable material, other component parts of the pad such as the film backing and adhesive tape fasteners are not in condition for reuse and at best contaminate the reusable fluff. Heretofore, any attempt to reuse the fluff or filler material has involved returning the entire pad, including the undesirable film backing and adhesive tape fastener components thereof to a recovery unit which tears the pad apart and returns all components thereof in comminuted form to the pad manufacturing machine. This results in a small percentage of film and adhesive tape particles in the filler for the next batch of pads and contaminates and reduces the quality of the filler material below that of virgin filler.

SUMMARY OF THE INVENTION

In accordance with the present invention, the undesirable components of otherwise waste pads, typically the backing film and adhesive tape fasteners, are not salvaged but are separated from the pad and are discarded. Only the filler material is recovered for salvage, thus maintaining high quality in the filler supply.

In accordance with the present invention, the waste pad is laid out flat and the cover sheet is cut open to expose the filler. The filler is then sucked from the pad, together with any fragments of the cover sheet. This useful material is returned to the pad fabricating machine and constitutes high quality filler material. The plastic backing and adhesive fastening tapes are collected and discharged to waste and do not return to the pad fabricating machine.

Other objects, features and advantages of the invention will appear from the disclosure hereof.

DESCRIPTION OF THE DRAWINGS

FIG. 1 is a plan view of apparatus embodying the present invention.

FIG. 2 is a side elevation of the apparatus of FIG. 1.

DESCRIPTION OF THE PREFERRED EMBODIMENT

Figure 3:
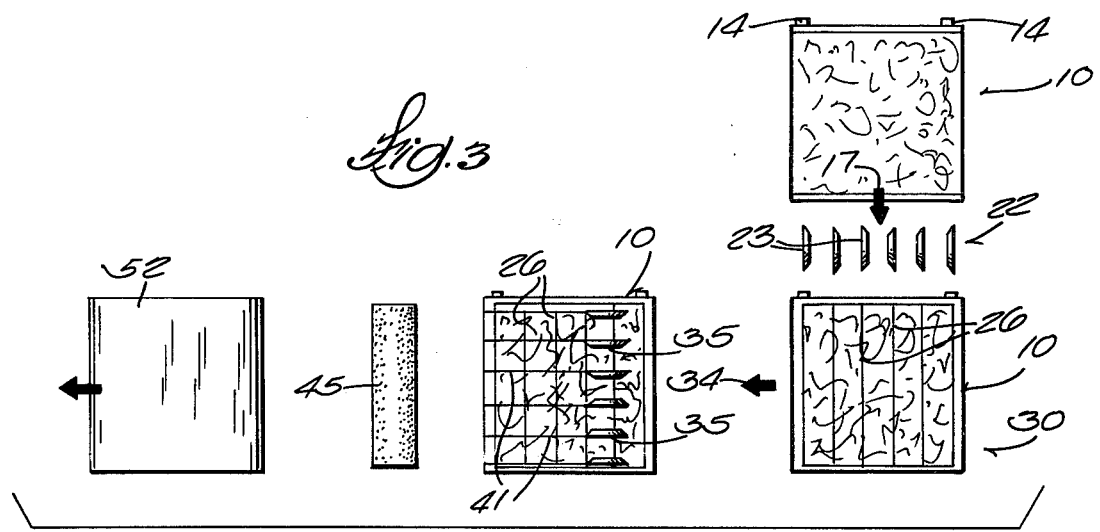
FIG. 3 is a schematic view similar to FIG. 1, but illustrating method steps.

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

In the disclosed embodiment, the pad 10 to be salvaged comprises a disposable diaper typically having a non-woven fabric cover sheet 11, a plastic film backing sheet 12 and an absorbent filler material 13 which typically comprises crepe wadding or cellulose fluff. Adhesive tape fasteners 14 may be applied at certain corners of the plastic film backing 12.

The pad fabricating machine is not shown in the drawings, but in typical installations an inspector will detect a defective pad 10 and will remove it from the pad fabricating machine and lay it out flat on a movable tray 15 which is mounted on slideways 16 on which the tray is movable in the direction of arrow 17.

Figure 4:
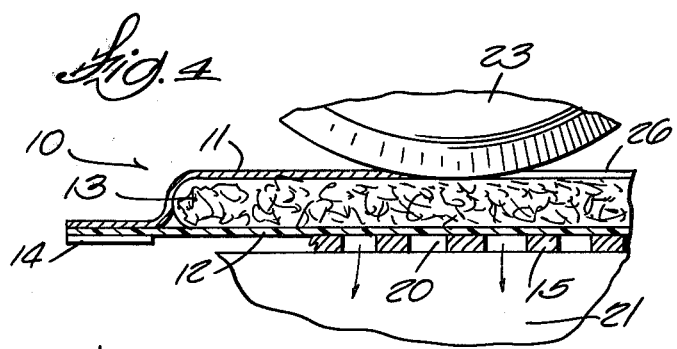
FIG. 4 is a fragmentary cross section taken along the line 4—4 of FIG. 1.

As best shown in FIG. 4, tray 15 is desirably provided with a series of perforations 20 through which pad 10 is exposed to the vacuum in a vacuum box 21. Vacuum box 21 is beyond the initial position of the tray 15 as it is shown in FIG. 1 and is beneath a first pad cover slitting mechanism 22. Slitter 22 comprises a set of ganged knife-edged wheels 23 which are mounted on a common shaft 24 driven by motor 25.

As tray 15 is advanced in the direction of arrow 17 beneath the first slitter 22, the subatmospheric pressure in the vacuum box 21 will hold the pad 10 securely against the tray 15, while the ganged knife-edged slitting wheels 23 will produce a series of longitudinal slits 26 (FIG. 3) in the pad cover 11.

After the longitudinal slits 26 are produced in the cover sheet 11 of the pad 10, the pad 10 is advanced further to its position indicated at 30 in FIG. 1 and FIG. 3, where it overlies a perforated belt 31 having perforations 42 traveling over a vacuum box 32. The ends of the perforated belt 31 are supported on end rolls 33.

The top run of belt 31 travels in the direction of arrow 34 (FIG. 1), transverse to the direction of arrow 17, and the partially slit pad 10 is transported thereon in said transverse direction to a second slitting mechanism 35. Slitting mechanism 35 also desirably comprises ganged knife-edged wheels 36 mounted within a vacuum hood 37 which has a discharge duct 40. Wheels 36 are powered by motor 38. The second slitter 35 will produce transverse slits 41 in the pad cover 11 to thoroughly open up the cover sheet 11 for vacuum removal of the fluff or filler material 13 from the pad into hood 37 and through the duct 40 to a recovery unit, now shown. As the suction in hood 37 is removing the filler material 13 from the pad, the plastic backing sheet 12 and adhesive tape fasteners 14 will be securely held by vacuum against the traveling perforated belt 31. Moreover, to securely hold the film backing 12 against dislocation, the pad 10 beneath hood 37 is held down at its side margins by traveling overhead belts 43 which are guided over end pulleys 44 to clamp the plastic backing sheet 12 against the perforated belt 31.

Figure 5:
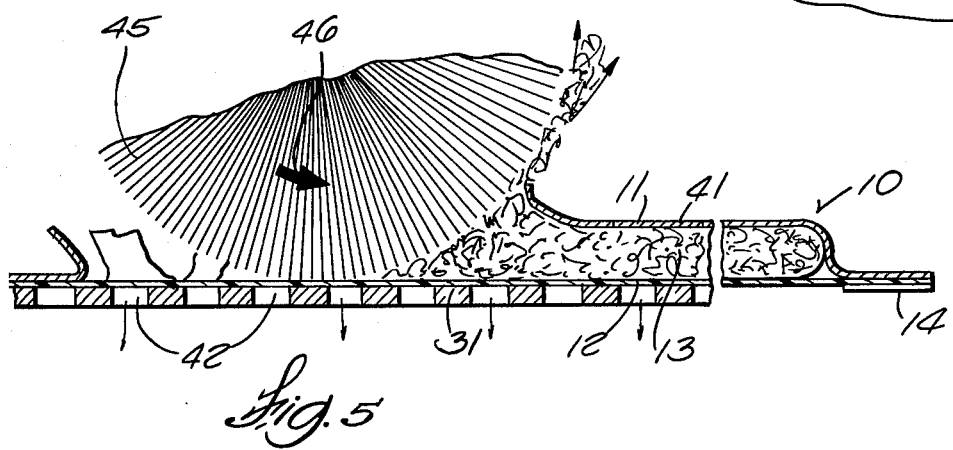
FIG. 5 is an enlarged fragmentary cross section taken along the line 5—5 of FIG. 1.

To assist the vacuum removal of the filler, hood 37 is also provided with a rotating brush 45 which rotates in the direction of arrow 46 in FIG. 5 and is mounted on a shaft 47. As indicated in FIG. 5, the brush 45 mechanically sweeps the filler material 13 from the pad 10 in the direction of arrows 50 into the air stream exhausted from hood 37 through duct 40.

The suction and sweeping apparatus will remove not only the filler material 13, but also any completely severed strips or portions of the cover sheet 11. Both of these components of the pad will be conveyed through duct 40 back to the filler supply for the pad fabrication machine. Both of these components constitute high quality filler material.

All that is left on the belt 31 is the plastic film backing 12, the adhesive tape fasteners 14 and any small fragments of filler material 13 and particles of cover sheet 11 which are not swept and sucked from the pad through the hood 37. The film backing sheet 12 and adhesive tape fasteners 14 then continue on the belt 31 to a discharge chute 51 where they are discharged to waste. An overhead belt 52 driven by motor 53 cooperates with the perforated belt 31 to ensure proper discharge of the waste to the chute 51.

What is claimed is:

1. Apparatus for recovering filler from a sanitary pad having a film backing and a cover sheet, said apparatus comprising:
   a movable tray on which the pad can be laid out flat,
   a cutter to which the movable tray will advance the pad to cut open the cover sheet to expose the filler,
   means for sucking the filler and the cut cover sheet from the film backing for salvage, and
   means for disposing of the film backing.

2. The apparatus of claim 1 in which the means for cutting open the cover to expose the filler comprises a first slitter to produce slits in one direction in the pad cover as it is advanced on said tray.

3. The apparatus of claim 2 in combination with a second slitter and means for advancing the slit pad in a direction transverse to the first direction by which the second slitter produces transverse slits in the cover.

4. The apparatus of claim 3 in which said first and second slitters comprise ganged knife-edge wheels.

5. Apparatus of claim 1 in further combination with means for sweeping the filler from the pad concurrently with sucking it therefrom.

6. The apparatus of claim 5 in which the means for sucking and the means for sweeping the pad are enclosed in a vacuum hood.

7. The apparatus of claim 6 in which the said hood is further provided with means for restraining the film backing against being swept and sucked as the pad travels therethrough.

* * * * *